(12) United States Patent
Rouet et al.

(10) Patent No.: US 11,998,385 B2
(45) Date of Patent: Jun. 4, 2024

(54) METHODS AND SYSTEMS FOR INVESTIGATING BLOOD VESSEL CHARACTERISTICS

(71) Applicant: KONINKLIJKE PHILIPS N.V., Eindhoven (NL)

(72) Inventors: Laurence Rouet, Paris (FR); Hernán Guillermo Morales Varela, Suresnes (FR); Constance Marie Anne Fourcade, Suresnes (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 313 days.

(21) Appl. No.: 17/423,871

(22) PCT Filed: Jan. 13, 2020

(86) PCT No.: PCT/EP2020/050617
§ 371 (c)(1),
(2) Date: Jul. 18, 2021

(87) PCT Pub. No.: WO2020/151965
PCT Pub. Date: Jul. 30, 2020

(65) Prior Publication Data
US 2022/0096048 A1 Mar. 31, 2022

(30) Foreign Application Priority Data
Jan. 24, 2019 (EP) .................................... 19290006

(51) Int. Cl.
*A61B 8/08* (2006.01)
*A61B 8/04* (2006.01)
(Continued)

(52) U.S. Cl.
CPC .............. *A61B 8/0891* (2013.01); *A61B 8/04* (2013.01); *A61B 8/145* (2013.01); *G06T 7/11* (2017.01);
(Continued)

(58) Field of Classification Search
CPC ......... A61B 8/0891; A61B 8/04; A61B 8/145; G06T 7/11; G06T 7/30; G06T 7/20; G06T 2207/10136; G06T 2207/30101
See application file for complete search history.

(56) References Cited

U.S. PATENT DOCUMENTS 5,997,479 A 12/1999 Savord
6,013,032 A 1/2000 Savord
(Continued)

FOREIGN PATENT DOCUMENTS

JP 2012024582 A 2/2012
JP 2017029786 A 2/2017

OTHER PUBLICATIONS

International Search Report and Written Opinion of PCT/EP2020/050617, dated May 26, 2020.
(Continued)

*Primary Examiner* — Dixomara Vargas (57) ABSTRACT

The invention provides a method for generating a non-invasive measure of blood vessel rigidity for a subject. The method includes obtaining 2D ultrasound data and 3D ultrasound data of the blood vessel from a given measurement location. The 2D ultrasound data provides information relating to a movement of the blood vessel and the 3D ultrasound data provides information relating to a shape of the blood vessel. A motion of the blood vessel is then determined based on the movement of the blood vessel. The method then includes providing the determined motion of the blood vessel, the shape of the blood vessel and an (Continued)

obtained non-invasive pressure measurement to a biomechanical model. A measure of rigidity is then determined based on the biomechanical model.

20 Claims, 7 Drawing Sheets

(51) Int. Cl.
*A61B 8/14* (2006.01)
*G06T 7/11* (2017.01)
*G06T 7/20* (2017.01)
*G06T 7/30* (2017.01)

(52) U.S. Cl.
CPC ............... *G06T 7/20* (2013.01); *G06T 7/30* (2017.01); *G06T 2207/10136* (2013.01); *G06T 2207/30101* (2013.01)

(56) References Cited

U.S. PATENT DOCUMENTS

| | | | |
|---|---|---|---|
| 6,283,919 B1 | 9/2001 | Roundhill | |
| 6,443,896 B1 | 9/2002 | Detmer | |
| 6,458,083 B1 | 10/2002 | Jago | |
| 6,530,885 B1 | 3/2003 | Entrekin | |
| 6,623,432 B2 | 9/2003 | Powers | |
| 8,768,019 B2 * | 7/2014 | Neidert | A61B 90/36 600/424 |
| 2007/0038084 A1 * | 2/2007 | Burla | A61B 8/481 600/437 |
| 2009/0099447 A1 | 4/2009 | De Korte | |
| 2009/0163785 A1 * | 6/2009 | Nelson | A61B 5/0059 600/322 |
| 2009/0299185 A1 | 12/2009 | Oikawa | |
| 2010/0290679 A1 | 11/2010 | Gasser | |
| 2011/0077518 A1 | 3/2011 | Miyachi | |
| 2012/0022843 A1 | 1/2012 | Ionasec | |
| 2012/0283564 A1 | 11/2012 | Ebbini | |
| 2015/0201910 A1 | 7/2015 | Zhao | |
| 2015/0245776 A1 * | 9/2015 | Hirohata | A61B 6/5217 600/504 |
| 2015/0356734 A1 * | 12/2015 | Ooga | A61B 6/486 382/131 |
| 2016/0199029 A1 | 7/2016 | Struijk | |
| 2017/0071479 A1 * | 3/2017 | Kano | A61B 5/026 |
| 2018/0070915 A1 | 3/2018 | Miyachi | |
| 2020/0126219 A1 * | 4/2020 | Wang | A61B 8/463 |
| 2022/0148735 A1 * | 5/2022 | Shige | G16H 30/40 |

OTHER PUBLICATIONS

Van Visseldorp, E.M.J. et al "Quantification of Aortic Stiffness and Wall Stress in Healthy Volunteers and Abdominal Aortic Aneurysm Patients using Time-Resolved 3D Ultrasound: A Comparison Study", European Heart Journal Cardiovascular Imaging, vol. 31, Jun. 2018, pp. 1-7.

Rouet, Laurence et al "A Minimally Interactive and Reproducible Method for Abdominal Aortic Aneurysm Quantification in 3D Ultrasound and Computed Tomography with Implicit Template Deformations", Computerized Medical Imaging and Graphics, vol. 58, 2017, pp. 75-85.

Van Visseldorp, E.M.J. et al "Patient Specific Wall Stress Analysis and Mechanical Characterization of Abdominal Aortic Aneurysms Using 4D Ultrasound," European Journal Vascuarl and Endovascular Surgery, vol. 52, No. 5, pp. 635-642, 2016.

Wittek, A. et al "A finite element updating approach for identification of the anisotropic hyperelastic properties of normal and diseased aortic walls from 4D ultrasound strain imaging," J. Mech. Behav. Biomed. Mater., No. Jun. 2015.

Gasser, T. Christian "Biomechanical Rupture Risk Assessment", Aorta, Apr. 2016, vol. 4, Issue 2, pp. 42-60.

Raghavan, M.L. et al "Wall Stress Distribution on Three-Dimensionally Reconstructed Models of human Abdominal Aortic Aneurysm", Journal of Vascular Surgery, vol. 31, No. 4, pp. 760-769, 2000.

Bihari, P. et al "Strain Measurement of Abdominal Aortic Aneurysm with Real-Time 3D Ultrasound Speckle Tracking", European Journal of Vascular and Endovascular Surgery, vol. 45, Issue 4, Apr. 2013.

* cited by examiner

METHODS AND SYSTEMS FOR INVESTIGATING BLOOD VESSEL CHARACTERISTICS

CROSS-REFERENCE TO PRIOR APPLICATIONS

This application is the U.S. National Phase application under 35 U.S.C. § 371 of International Application No. PCT/EP2020/050617, filed on Jan. 13, 2020, which claims the benefit of European Patent Application No. 19290006.6, filed on Jan. 24, 2019. These applications are hereby incorporated by reference herein.

FIELD OF THE INVENTION

The invention relates to the field of ultrasound, and in particular the field of investigating blood vessel characteristics using ultrasound.

BACKGROUND OF THE INVENTION

Aortic abdominal aneurysms (AAAs) are a pathological and irreversible deformation of the arterial wall. Currently, the AAA rupture risk is based on aneurysm size (above 55 mm in diameter) and growth rate (1 cm/year). However, it is known that these criteria are not sufficient to prevent all risks of rupture. In roughly 10% of cases, AAA will rupture despite being below the size or growth criteria. In addition, it is possible that some unnecessary interventions are performed in order to assess the AAA, which is inefficient in terms of patient management and costs. Therefore, additional information is required to quantify the status of the arterial wall prior to rupture.

An estimation of the blood vessel wall stiffness is a natural biomarker since the rupture of the vessel wall will occur when the wall stress exceeds the wall strength. To estimate wall stress and to characterize the blood vessel wall, a constitutive law of the material needs to be provided. It has been shown that blood vessel walls harboring aneurysms are stiffer than normal aortas, with a lower yield stress (point of fiber rupture).

Currently, several methods are employed with the aim to retrieve a material stiffness of the blood vessel wall, as well as provide additional criteria to predict the risk of rupture based on vascular imaging.

Such methods typically include the use of computerized tomography (CT) or magnetic resonance imaging (MRI) data to model the wall of the blood vessel.

In comprehensive wall modelling, electrocardiogram (ECG)-gated CT and MRI are the preferred imaging modalities with constitutive laws with up to 6 parameters. These approaches target the most realistic modelling of the vascular structures. Such methods require a large amount of processing power and expensive imaging equipment.

Simpler wall modelling methods exist, which use parameter estimates based on gender, age and computed tomography angiography (CTA). In this case, the constitutive laws require fewer parameters based on simplifying hypotheses. Such methods are less accurate and may result in a poor quality estimate of the vessel wall stiffness.

In another method, ultrasound imaging is used to explore the stiffness of the blood vessel. Such methods require two inputs from the patient: 4D ultrasound data; and brachial pressure. Due to the poor temporal resolution of 4D ultrasound and the computational power required to process it, the implementation of such methods may be impractical and unreliable in a clinical setting.

There is therefore a need for a means of assessing the characteristics of a blood vessel in an accurate and efficient manner.

US 2018/070915 discloses a method of simultaneously displaying an inter media thickness and elastic indices of a vessel in order to assess a risk of developing arteriosclerosis.

US 2009/099447 discloses a method for generating hardness and/or strain information of a tissue based on reflected ultrasound signals received from the tissue.

US 2012/283564 discloses a method for measuring vessel wall tissue motion and deformation based on two dimensional speckle tracking.

US 2009/299185 discloses the use of multiple ultrasound probes to investigate a region of interest and a signal delay scheme for aligning the data acquired from each probe.

US 2012/022843 discloses a method of generating a model of a cardiac system of a subject based on acquired ultrasound data.

US 2016/199029 discloses an ultrasound probe having a plurality of transducer arrays arranged in order to focus the ultrasound beams at a desired location.

JP 2012024582 discloses an imaging system adapted to autofocus based on a touch input of the user.

SUMMARY OF THE INVENTION

The invention is defined by the claims.

According to examples in accordance with an aspect of the invention, there is provided a method for generating a non-invasive measure of blood vessel rigidity for a subject, the method comprising:

obtaining 2D ultrasound data of a blood vessel from a first measurement location, wherein the 2D ultrasound data provides information relating to a movement of the blood vessel;

obtaining 3D ultrasound data of the blood vessel from the first measurement location, wherein the 3D ultrasound data provides information relating to a 3D geometry of the blood vessel;

determining a motion of the blood vessel based on the movement of the blood vessel from the 2D ultrasound data;

obtaining a non-invasive pressure measurement from the subject;

providing the determined motion of the blood vessel, the shape of the blood vessel and the non-invasive pressure measurement to a biomechanical model; and generating a measure of rigidity based on the biomechanical model.

The method provides for the generating of a non-invasive measure of blood vessel rigidity.

The 2D ultrasound data provides a high temporal resolution data set for a blood vessel. In this way, the 2D ultrasound data accurately represents the movement of the blood vessel.

The 3D ultrasound data provides an accurate representation of the blood vessel geometry. As the 3D ultrasound data is acquired at the same location as the 2D ultrasound data, the two data sets are already spatially registered with each other.

The combination of the 2D ultrasound data and the 3D ultrasound data results in the movement information conveyed by the 2D ultrasound data being combined with the geometry information conveyed by the 3D ultrasound data, meaning that an accurate representation of the 3D motion of the blood vessel may be generated.

The blood vessel motion, and the vessel shape, are then provided, with a pressure measurement, to a biomechanical model for generating a measure of blood vessel rigidity.

In an embodiment, the 2D ultrasound data comprises bi-plane ultrasound data, wherein the bi-plane ultrasound data comprises:
- a first data plane representing a first orientation; and
- a second data plane representing a second orientation, the second orientation being orthogonal to the first orientation.

In this way, the 2D ultrasound data may represent a blood vessel cross section and a longitudinal view along the length of the blood vessel, thereby recording the motion of the blood vessel in two orientations. This increases the accuracy of the final measure of blood vessel rigidity.

In an embodiment, the 2D ultrasound data comprises a plurality of data planes each representing a different location along a length of the blood vessel, wherein each data plane represents a blood vessel cross section.

In this way, the measure of blood vessel rigidity may include multiple localized rigidity measurements, thereby providing a more detailed measure of blood vessel rigidity.

In an arrangement, the method further comprises:
- obtaining additional 2D ultrasound data and/or additional 3D ultrasound data of a blood vessel from a second measurement location; and
- comparing the 2D ultrasound data and/or 3D ultrasound data to the additional 2D ultrasound data and/or additional 3D ultrasound data.

In this way, the ultrasound data may be compared to that of another blood vessel, for example a healthy blood vessel, in order to provide a reference point for the condition of the blood vessel of interest.

In an embodiment, the method further comprises generating a cineloop of the blood vessel based on the 2D ultrasound data, wherein the cineloop comprises a plurality of ultrasound image frames of the blood vessel, each acquired at a different moment during a cardiac cycle.

In this way, a representation of the movement of the blood vessel over time may be generated. For example, the cineloop may represent one or more complete cardiac cycles.

In a further embodiment, the method further comprises:
- applying a tracking algorithm to the cineloop, thereby delineating an initial blood vessel border for at least one of the plurality of ultrasound image frames of the blood vessel;
- for each of the plurality of ultrasound image frames, determining a blood vessel border based on the initial blood vessel border; and
- determining a blood vessel wall displacement over time based on the plurality of blood vessel borders.

In this way, the movement of the blood vessel walls over time may be measured.

In an embodiment, the method further comprises determining a maximum blood vessel wall displacement and/or an average blood vessel wall displacement based on the blood vessel wall displacement over time.

In an arrangement, the method further comprises performing a spatial registration on the obtained 2D ultrasound data, and wherein the obtaining of the 3D ultrasound data is based on the spatial registration.

In this way, any unintentional movement of the ultrasound probe may be corrected between the acquisition of the 2D ultrasound data and the 3D ultrasound data.

In an embodiment, the method further comprises segmenting a representation of the 3D structure of the blood vessel from the 3D ultrasound data.

In this way, the 3D geometry of the blood vessel may be extracted from the 3D ultrasound data.

In an arrangement, the non-invasive pressure measurement comprises a brachial pressure index.

In an embodiment, the generating of a measure of rigidity based on the biomechanical model comprises:
- generating a test blood vessel rigidity;
- simulating a test motion of the blood vessel based on the test blood vessel rigidity;
- comparing the test motion of the blood vessel to the motion of the blood vessel;
- if the test motion of the blood vessel matches the motion of the blood vessel, selecting the test blood vessel rigidity as the measure of rigidity; and
- if the test motion of the blood vessel does not match the motion of the blood vessel, adjusting the test blood vessel rigidity.

In this way, the biomechanical model may iteratively test the rigidity of the blood vessel in order to converge on the true rigidity based on the measured movement of the blood vessel.

According to examples in accordance with an aspect of the invention, there is provided a computer program comprising computer program code means which is adapted, when said computer program is run on a computer, to implement the method described above.

According to examples in accordance with an aspect of the invention, there is provided a processing unit, wherein the processing unit is adapted to:
- obtain 2D ultrasound data of a blood vessel from a first measurement location, wherein the 2D ultrasound data provides information relating to a movement of the blood vessel;
- obtain 3D ultrasound data of the blood vessel from the first measurement location, wherein the 3D ultrasound data provides information relating to a 3D geometry of the blood vessel;
- determine a motion of the blood vessel based on the movement of the blood vessel from the 2D ultrasound data;
- obtain a non-invasive pressure measurement;
- provide the determined motion of the blood vessel, the shape of the blood vessel and the non-invasive pressure measurement to a biomechanical model; and
- generate a measure of rigidity based on the biomechanical model.

According to examples in accordance with an aspect of the invention, there is provided an ultrasound system, the system comprising:
- a processing unit as described above; and
- an ultrasound probe, wherein the ultrasound probe is adapted to acquire the 2D ultrasound data and wherein the probe is further adapted to acquire the 3D ultrasound data.

In an embodiment, the system further comprises a pressure measurement device adapted to acquire the non-invasive pressure measurement.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a method for generating a non-invasive measure of blood vessel rigidity for a subject. The method includes obtaining 2D ultrasound data and 3D ultrasound data of the blood vessel from a given measurement location. The 2D ultrasound data provides information relating to a movement of the blood vessel and the 3D ultrasound data provides information relating to a shape of the blood vessel. A motion of the blood vessel is then determined based on the movement of the blood vessel. The method then includes providing the determined motion of the blood vessel, the shape of the blood vessel and an obtained non-invasive pressure measurement to a biomechanical model. A measure of rigidity is then determined based on the biomechanical model.

Figure 1:
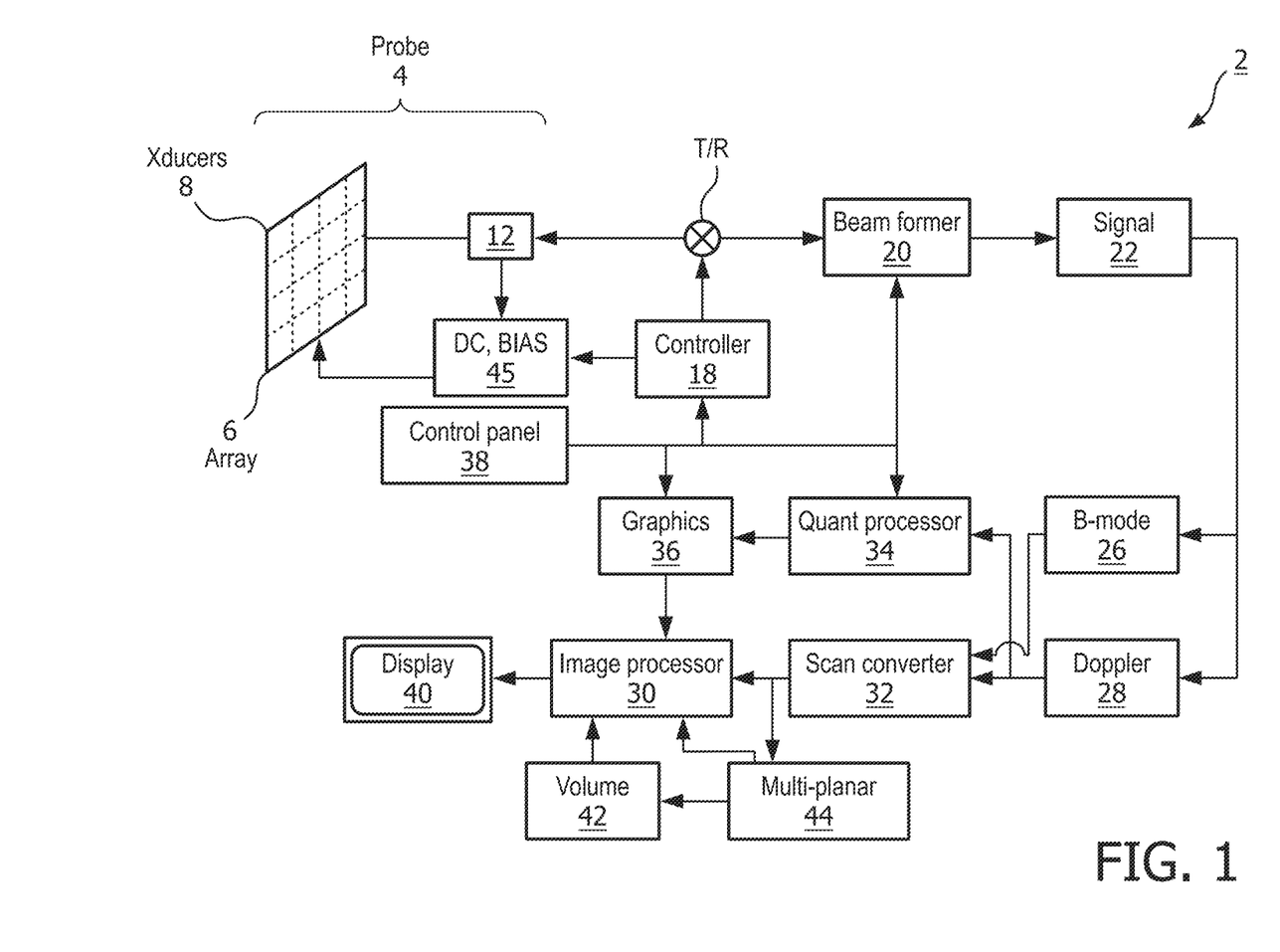
FIG. 1 shows an ultrasound diagnostic imaging system to explain the general operation.

The general operation of an exemplary ultrasound system will first be described, with reference to FIG. 1, and with emphasis on the signal processing function of the system since this invention relates to the processing of the signals measured by the transducer array.

The system comprises an array transducer probe 4 which has a transducer array 6 for transmitting ultrasound waves and receiving echo information. The transducer array 6 may comprise CMUT transducers; piezoelectric transducers, formed of materials such as PZT or PVDF; or any other suitable transducer technology. In this example, the transducer array 6 is a two-dimensional array of transducers 8 capable of scanning either a 2D plane or a three dimensional volume of a region of interest. In another example, the transducer array may be a 1D array.

The transducer array 6 is coupled to a microbeamformer 12 which controls reception of signals by the transducer elements. Microbeamformers are capable of at least partial beamforming of the signals received by sub-arrays, generally referred to as "groups" or "patches", of transducers as described in U.S. Pat. No. 5,997,479 (Savord et al.), U.S. Pat. No. 6,013,032 (Savord), and U.S. Pat. No. 6,623,432 (Powers et al.).

It should be noted that the microbeamformer is entirely optional. Further, the system includes a transmit/receive (T/R) switch 16, which the microbeamformer 12 can be coupled to and which switches the array between transmission and reception modes, and protects the main beamformer 20 from high energy transmit signals in the case where a microbeamformer is not used and the transducer array is operated directly by the main system beamformer. The transmission of ultrasound beams from the transducer array 6 is directed by a transducer controller 18 coupled to the microbeamformer by the T/R switch 16 and a main transmission beamformer (not shown), which can receive input from the user's operation of the user interface or control panel 38. The controller 18 can include transmission circuitry arranged to drive the transducer elements of the array 6 (either directly or via a microbeamformer) during the transmission mode.

In a typical line-by-line imaging sequence, the beamforming system within the probe may operate as follows. During transmission, the beamformer (which may be the microbeamformer or the main system beamformer depending upon the implementation) activates the transducer array, or a sub-aperture of the transducer array. The sub-aperture may be a one dimensional line of transducers or a two dimensional patch of transducers within the larger array. In transmit mode, the focusing and steering of the ultrasound beam generated by the array, or a sub-aperture of the array, are controlled as described below.

Upon receiving the backscattered echo signals from the subject, the received signals undergo receive beamforming (as described below), in order to align the received signals, and, in the case where a sub-aperture is being used, the sub-aperture is then shifted, for example by one transducer element. The shifted sub-aperture is then activated and the process repeated until all of the transducer elements of the transducer array have been activated.

For each line (or sub-aperture), the total received signal, used to form an associated line of the final ultrasound image, will be a sum of the voltage signals measured by the transducer elements of the given sub-aperture during the receive period. The resulting line signals, following the beamforming process below, are typically referred to as radio frequency (RF) data. Each line signal (RF data set) generated by the various sub-apertures then undergoes additional processing to generate the lines of the final ultrasound image. The change in amplitude of the line signal with time will contribute to the change in brightness of the ultrasound image with depth, wherein a high amplitude peak will correspond to a bright pixel (or collection of pixels) in the final image. A peak appearing near the beginning of the line signal will represent an echo from a shallow structure, whereas peaks appearing progressively later in the line signal will represent echoes from structures at increasing depths within the subject.

One of the functions controlled by the transducer controller 18 is the direction in which beams are steered and focused. Beams may be steered straight ahead from (orthogonal to) the transducer array, or at different angles for a wider field of view. The steering and focusing of the transmit beam may be controlled as a function of transducer element actuation time.

Two methods can be distinguished in general ultrasound data acquisition: plane wave imaging and "beam steered" imaging. The two methods are distinguished by a presence of the beamforming in the transmission ("beam steered" imaging) and/or reception modes (plane wave imaging and "beam steered" imaging).

Looking first to the focusing function, by activating all of the transducer elements at the same time, the transducer array generates a plane wave that diverges as it travels through the subject. In this case, the beam of ultrasonic waves remains unfocused. By introducing a position dependent time delay to the activation of the transducers, it is possible to cause the wave front of the beam to converge at a desired point, referred to as the focal zone. The focal zone is defined as the point at which the lateral beam width is less than half the transmit beam width. In this way, the lateral resolution of the final ultrasound image is improved.

For example, if the time delay causes the transducer elements to activate in a series, beginning with the outermost elements and finishing at the central element(s) of the transducer array, a focal zone would be formed at a given distance away from the probe, in line with the central element(s). The distance of the focal zone from the probe will vary depending on the time delay between each subsequent round of transducer element activations. After the beam passes the focal zone, it will begin to diverge, forming the far field imaging region. It should be noted that for focal zones located close to the transducer array, the ultrasound beam will diverge quickly in the far field leading to beam width artifacts in the final image. Typically, the near field, located between the transducer array and the focal zone, shows little detail due to the large overlap in ultrasound beams. Thus, varying the location of the focal zone can lead to significant changes in the quality of the final image.

It should be noted that, in transmit mode, only one focus may be defined unless the ultrasound image is divided into multiple focal zones (each of which may have a different transmit focus).

In addition, upon receiving the echo signals from within the subject, it is possible to perform the inverse of the above described process in order to perform receive focusing. In other words, the incoming signals may be received by the transducer elements and subject to an electronic time delay before being passed into the system for signal processing. The simplest example of this is referred to as delay-and-sum beamforming. It is possible to dynamically adjust the receive focusing of the transducer array as a function of time.

Looking now to the function of beam steering, through the correct application of time delays to the transducer elements it is possible to impart a desired angle on the ultrasound beam as it leaves the transducer array. For example, by activating a transducer on a first side of the transducer array followed by the remaining transducers in a sequence ending at the opposite side of the array, the wave front of the beam will be angled toward the second side. The size of the steering angle relative to the normal of the transducer array is dependent on the size of the time delay between subsequent transducer element activations.

Further, it is possible to focus a steered beam, wherein the total time delay applied to each transducer element is a sum of both the focusing and steering time delays. In this case, the transducer array is referred to as a phased array.

In case of the CMUT transducers, which require a DC bias voltage for their activation, the transducer controller 18 can be coupled to control a DC bias control 45 for the transducer array. The DC bias control 45 sets DC bias voltage(s) that are applied to the CMUT transducer elements.

For each transducer element of the transducer array, analog ultrasound signals, typically referred to as channel data, enter the system by way of the reception channel. In the reception channel, partially beamformed signals are produced from the channel data by the microbeamformer 12 and are then passed to a main receive beamformer 20 where the partially beamformed signals from individual patches of transducers are combined into a fully beamformed signal, referred to as radio frequency (RF) data. The beamforming performed at each stage may be carried out as described above, or may include additional functions. For example, the main beamformer 20 may have 128 channels, each of which receives a partially beamformed signal from a patch of dozens or hundreds of transducer elements. In this way, the signals received by thousands of transducers of a transducer array can contribute efficiently to a single beamformed signal.

The beamformed reception signals are coupled to a signal processor 22. The signal processor 22 can process the received echo signals in various ways, such as: band-pass filtering; decimation; I and Q component separation; and harmonic signal separation, which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting noise at higher frequencies from greater depths that is typically devoid of anatomical information.

The beamformers for transmission and for reception are implemented in different hardware and can have different functions. Of course, the receiver beamformer is designed to take into account the characteristics of the transmission beamformer. In FIG. 1 only the receiver beamformers 12, 20 are shown, for simplicity. In the complete system, there will also be a transmission chain with a transmission micro beamformer, and a main transmission beamformer.

The function of the micro beamformer 12 is to provide an initial combination of signals in order to decrease the number of analog signal paths. This is typically performed in the analog domain.

The final beamforming is done in the main beamformer 20 and is typically after digitization.

The transmission and reception channels use the same transducer array 6 which has a fixed frequency band. However, the bandwidth that the transmission pulses occupy can vary depending on the transmission beamforming used. The reception channel can capture the whole transducer bandwidth (which is the classic approach) or, by using bandpass processing, it can extract only the bandwidth that contains the desired information (e.g. the harmonics of the main harmonic).

The RF signals may then be coupled to a B mode (i.e. brightness mode, or 2D imaging mode) processor 26 and a Doppler processor 28. The B mode processor 26 performs amplitude detection on the received ultrasound signal for the imaging of structures in the body, such as organ tissue and blood vessels. In the case of line-by-line imaging, each line (beam) is represented by an associated RF signal, the amplitude of which is used to generate a brightness value to be assigned to a pixel in the B mode image. The exact location of the pixel within the image is determined by the location of the associated amplitude measurement along the RF signal and the line (beam) number of the RF signal. B mode images of such structures may be formed in the harmonic or fundamental image mode, or a combination of both as described in U.S. Pat. No. 6,283,919 (Roundhill et al.) and U.S. Pat. No. 6,458,083 (Jago et al.) The Doppler processor 28 processes temporally distinct signals arising from tissue movement and blood flow for the detection of moving substances, such as the flow of blood cells in the image field. The Doppler processor 28 typically includes a wall filter with parameters set to pass or reject echoes returned from selected types of materials in the body.

The structural and motion signals produced by the B mode and Doppler processors are coupled to a scan converter 32 and a multi-planar reformatter 44. The scan converter 32 arranges the echo signals in the spatial relationship from which they were received in a desired image format. In other words, the scan converter acts to convert the RF data from a cylindrical coordinate system to a Cartesian coordinate system appropriate for displaying an ultrasound image on an image display 40. In the case of B mode imaging, the brightness of pixel at a given coordinate is proportional to the amplitude of the RF signal received from that location. For instance, the scan converter may arrange the echo signal into a two dimensional (2D) sector-shaped format, or a pyramidal three dimensional (3D) image. The scan converter can overlay a B mode structural image with colors corresponding to motion at points in the image field, where the Doppler-estimated velocities to produce a given color. The combined B mode structural image and color Doppler image depicts the motion of tissue and blood flow within the structural image field. The multi-planar reformatter will convert echoes that are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on an image display 40. The imaging processor may be adapted to remove certain imaging artifacts from the final ultrasound image, such as: acoustic shadowing, for example caused by a strong attenuator or refraction; posterior enhancement, for example caused by a weak attenuator; reverberation artifacts, for example where highly reflective tissue interfaces are located in close proximity; and so on. In addition, the image processor may be adapted to handle certain speckle reduction functions, in order to improve the contrast of the final ultrasound image.

In addition to being used for imaging, the blood flow values produced by the Doppler processor 28 and tissue structure information produced by the B mode processor 26 are coupled to a quantification processor 34. The quantification processor produces measures of different flow conditions such as the volume rate of blood flow in addition to structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40, and for audio output from the display device 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name. The user interface is also coupled to the transmit controller 18 to control the generation of ultrasound signals from the transducer array 6 and hence the images produced by the transducer array and the ultrasound system. The transmit control function of the controller 18 is only one of the functions performed. The controller 18 also takes account of the mode of operation (given by the user) and the corresponding required transmitter configuration and band-pass configuration in the receiver analog to digital converter. The controller 18 can be a state machine with fixed states.

The user interface is also coupled to the multi-planar reformatter 44 for selection and control of the planes of multiple multi-planar reformatted (MPR) images which may be used to perform quantified measures in the image field of the MPR images.

Figure 2:
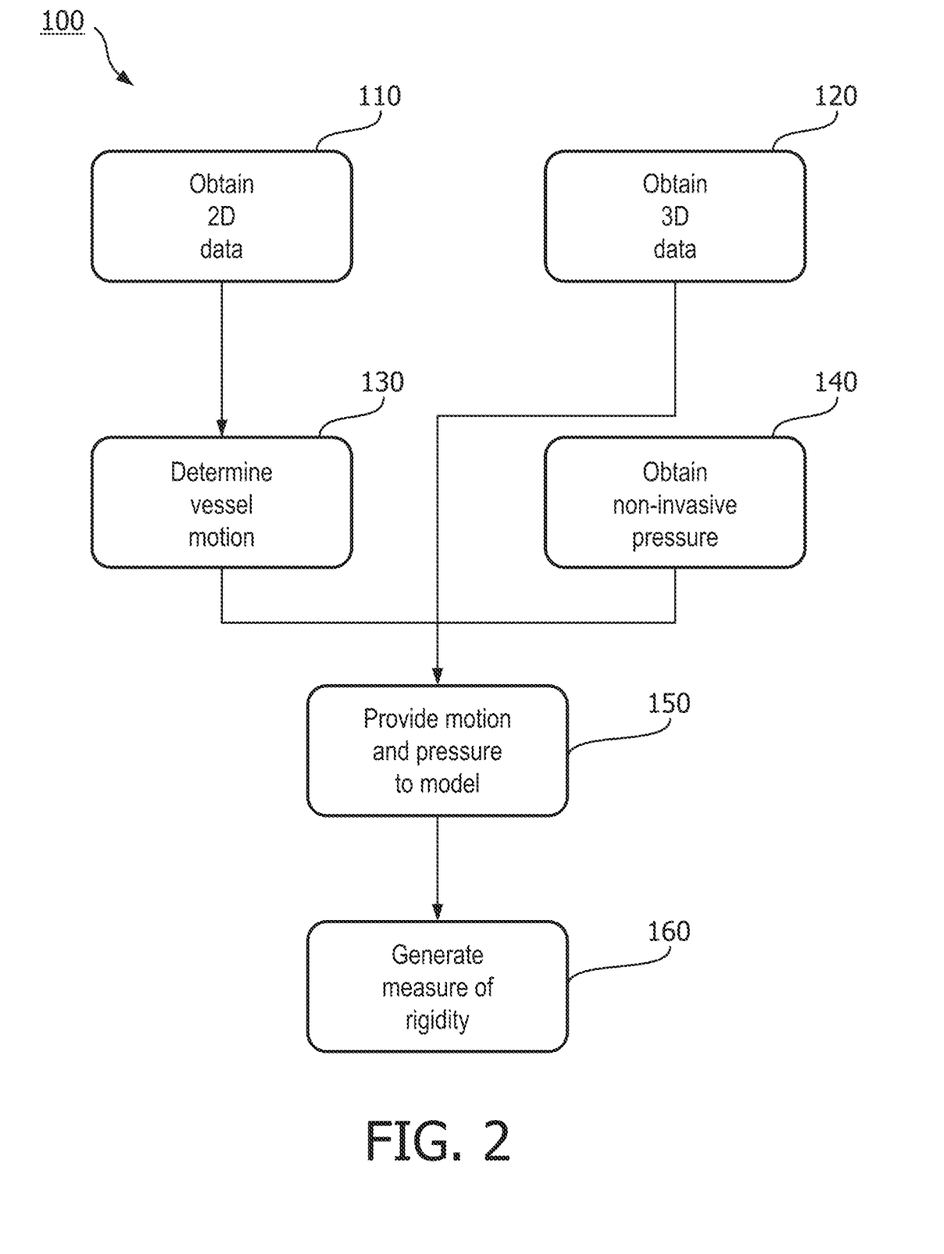
FIG. 2 shows a method of the invention.

FIG. 2 shows a method 100 for generating a non-invasive measure of blood vessel rigidity for a subject.

The method begins in step 110 where 2D ultrasound data of a blood vessel is obtained from a measurement location. The 2D ultrasound data may be obtained using an ultrasound probe such as the one described above with reference to FIG. 1.

The 2D ultrasound data may be acquired over a period of time, for example, over several cardiac cycles. Due to the high temporal resolution of the 2D ultrasound data, the 2D ultrasound data conveys accurate information relating to the movement of the blood vessel over time. In other words, the change in shape of the blood vessel (i.e. the expansion and contraction over a cardiac cycle) may be extracted from the 2D ultrasound data.

The 2D ultrasound data may include bi-plane ultrasound data. For example, a first plane of the bi-plane ultrasound data may include a cross sectional view of the blood vessel, which may be circular or elliptical, and the second plane may represent a longitudinal view of the blood vessel.

Further, the 2D ultrasound data may represent a plurality of data planes each representing a different location along a length of the blood vessel, wherein each data plane represents a blood vessel cross section.

In other words, the ultrasound probe may acquire multiple axial planes for a given longitudinal, or measurement, position. Using these multiples planes, the method may provide local rigidity estimates at various locations along the vessel. In this way, changes in the local rigidity of a vessel may be identified and assessed.

For example, 2D bi-plane imaging of the vessel may be performed. In this way, it may be checked that the probe orientation is well aligned with the main axis of the vessel (along its length). By optimizing the axial and longitudinal views (orthogonal to the main axis and in line with the main axis, respectively), the image quality of the vessel borders, together with the quality of subsequent motion estimation, may be improved.

In a further example, the 2D ultrasound data may be acquired at various distal locations to obtain a series of local quantifications. By way of example, this may be employed for subjects having small aneurysms as the diseased segment of the blood vessel may be compared against a heathy portion. In addition, a combination of multiple rigidity estimates from various ultrasound data acquisitions may be used to improve the quality of the rigidity estimate, and further in an assessment of aneurism rupture risk.

An estimate of the vessel properties at another location may provide comparative information to the biomechnical model, for example between a healthy and a diseased section of a vessel. The biomechanical properties may then be estimated for both locations and the obtained properties compared.

In addition to obtaining 2D ultrasound data, the method includes obtaining 3D ultrasound data of the blood vessel in step 120. The 3D ultrasound data is obtained from the same measurement location as the 2D ultrasound data, for example, by not moving the ultrasound probe between acquisitions. The 3D ultrasound data provides information relating to a shape of the blood vessel.

Thus, across steps 110 and 120, two ultrasound data acquisitions are performed. The first acquisition is for obtaining the 2D ultrasound data and the second acquisition is for obtaining the 3D ultrasound data acquisition, both of which are acquired at the same measurement location. The 3D ultrasound data represents the blood vessel geometry in 3D and is already spatially registered with the 2D planes, as it is acquired from the same measurement location.

The method may include a spatial registration step adapted to check the spatial registration of the 2D ultrasound data and the 3D ultrasound data and correct any unintentional movement of the ultrasound probe between acquisitions. For example, a magnetic tracker may be used to spatially register the 2D and 3D data acquisitions. The spatial registration may be performed between the obtaining of the 2D ultrasound data and the obtaining of the 3D ultrasound data.

Thus, the method ensures a correspondence between the 2D ultrasound data and the 3D ultrasound data, so that the movements of the blood vessel may be registered in the 3D space.

In step 130, the motion of the blood vessel is determined based on the movement of the blood vessel (extracted from the 2D ultrasound data). Independently, the shape of the blood vessel (extracted from the 3D ultrasound data) is obtained. An example of the determination of the motion of the blood vessel is described further below with reference to FIG. 3.

In step 140, a non-invasive pressure measurement is obtained from the subject.

The pressure measurement may be obtained by way of any suitable non-invasive measurement means. For example, the non-invasive pressure measurement may comprise a brachial pressure index. In this case, the pressure measurement may be obtained by way of a blood pressure cuff. The non-invasive pressure measurement may be used to estimate the internal pressure of the blood vessel.

In step 150, the determined motion of the blood vessel and the non-invasive pressure measurement is provided to a biomechanical model.

In step 160, a measure of rigidity is generated based on the biomechanical model. The rigidity measure may be used in a number of applications, such as the assessment of rupture risk for an aneurism. The model may operate based on a single parameter, such as vessel rigidity, or multiple parameters. An example of the generating of the measure of rigidity using a biomechanical model is described further below with reference to FIG. 4.

The generating of the measure of rigidity based on a combination of 2D ultrasound data and 3D ultrasound data provides a number of benefits over typical methods.

For example, bi-plane 2D ultrasound data may be acquired at a frequency of 30 Hz; whereas 4D ultrasound data, which is typically used in the assessment of blood vessel rigidity, is limited to a frequency of 4-8 Hz as shown in E. M. J. van Disseldorp et al, "Quantification of aortic stiffness and wall stress in healthy volunteers and abdominal aortic aneurysm patients using time-resolved 3D ultrasound: a comparison study," *Eur. Hear. J.—Cardiovasc. Imaging*, vol. 31, no. June, pp. 1-7, 2018.

The same poor temporal resolution limits apply to the use of ECG-gated CT, a common alternative to 4D ultrasound data. The insufficient temporal resolution of both methods can lead to an underestimation of the wall dilatation as systolic and diastolic phases may not be captured. This problem cannot be solved by acquiring several cardiac cycles, because long acquisitions are often not feasible in subjects (particularly diseased or elderly subjects) due to the need for holding the breath during acquisition. Missing the amplitude of the vessel wall motion in this way leads to an underestimation of the tissue properties (which corresponds to stiffer material) and to a decreased risk of rupture estimate.

In addition, the achievable spatial resolution of bi-plane 2D ultrasound imaging is significantly higher than that of 4D ultrasound imaging. Thus, the use of 2D ultrasound data greatly improves the precision of the vessel movement measurements and has a direct impact on the biomechanical characterization of the vessel tissue. Further, all volumes in a 4D ultrasound sequence would need to be registered, thereby affecting the precision of local displacement estimation.

Further, the typical methods of ECG-gated CT and 4D ultrasound imaging operate on the assumption of homogenous material distribution, meaning that a sole parameter is obtained for the whole blood vessel, regardless of healthy or diseased segments of the vessel. In the case of small aneurysms, a lower estimate of blood vessel stiffness may be obtained due to the healthy vessel segments, thereby obtaining an inaccurate quantification of vessel stiffness in the critical zones where the unhealthy tissue is located. The use of 2D ultrasound data, and more specifically the 2D data acquisition planes, provides for local material estimations, thereby allowing for a heterogeneous material description when several planes are used.

Figure 3:
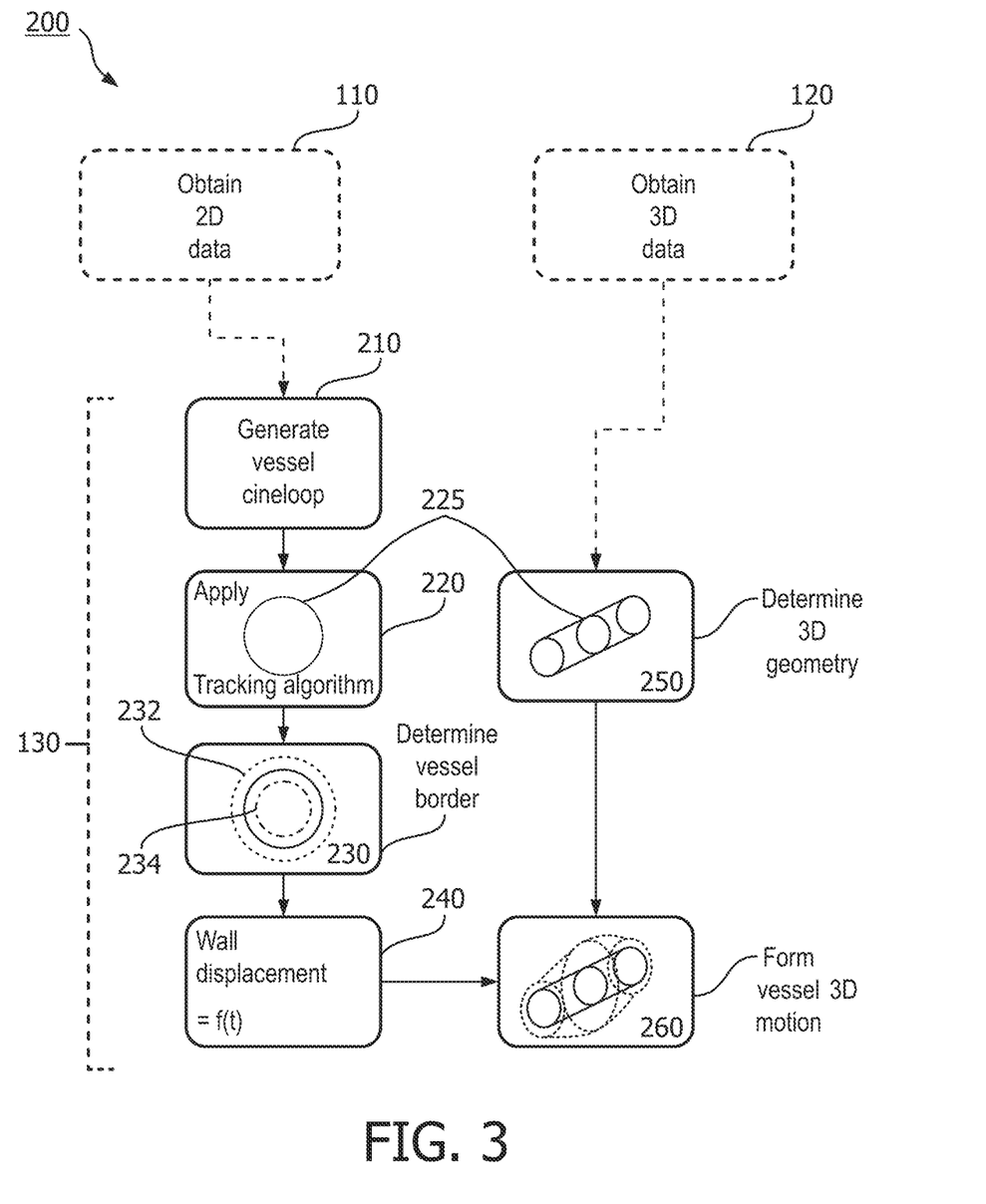
FIG. 3 shows a method for determining the motion of a blood vessel.

FIG. 3 shows a method 200 for determining the motion of a blood vessel. This method may be employed as step 130 in FIG. 2 as described above.

The method begins in step 210, wherein a cineloop of the blood vessel is generated based on the 2D ultrasound data. A cineloop is a set of images that contains a sequence of individual frames. In the case of high acquisition frame rates, the cineloop may contain more frames than would be displayed during a conventional examination. In this example, the cineloop comprises a plurality of ultrasound image frames of the blood vessel.

In step 220, a tracking algorithm is applied to the cineloop. The tracking algorithm is adapted to delineate, or identify, an initial blood vessel border for at least one of the plurality of ultrasound image frames of the blood vessel.

For example, the cineloop comprises a plurality of image frames showing a cross section 225 of the blood vessel, the tracking algorithm may identify said cross section within a given image frame.

In step 230, for each of the plurality of ultrasound image frames, the blood vessel border is determined based on the initial blood vessel border. In other words, the borders of the vessel may be determined for each image frame. For example, the vessel borders may expand 232 or contract 234 across the plurality of ultrasound images of the cineloop.

Put another way, the delineation of the initial vessel boarder may be propagated automatically onto all the of the ultrasound image frames of the cineloop. The tracking algorithm may be performed in both the axial views and the longitudinal views. The axial tracking may provide the majority of the motion information regarding vessel dilation during a cardiac cycle; whereas, the longitudinal tracking may be used to correct for any longitudinal motion occurring during the cardiac cycle.

In step 240, the blood vessel wall displacement over time is determined based on the plurality of blood vessel borders. Further, a maximum blood vessel wall displacement and/or an average blood vessel wall displacement may be determined. In other words, the cineloop is used to extract vascular motion.

For example, using the results of the tracking algorithm, one cardiac cycle may be identified where the diastole and systole correspond to the maximum amplitude of vessel motion. Using the selected cardiac cycle, the vessel motion at the measurement location may be computed. The motion can be the motion between diastole and systole, or a model with multiple time samples during the cardiac cycle due to the high temporal resolution of the 2D ultrasound data.

Alternatively, the results of the tracking algorithm may be averaged using the amplitude of vessel motion from multiple cardiac cycles.

In step 250, the 3D geometry of the vessel is determined from the 3D ultrasound data captured from the same location as the 2D ultrasound data. Once again, the capturing of the 2D ultrasound data and the 3D ultrasound data from the same location ensures that the 2D ultrasound images and 3D ultrasound images can be processed in a common coordinate system for the biomechanical simulation of the vessel. The 3D geometry may be segmented using, for example, a 3D segmentation algorithm as discussed in L. Rouet et al, "A Minimally Interactive and Reproducible Method for Abdominal Aortic Aneurysm Quantification in 3D Ultrasound and Computed Tomography with Implicit Template Deformations", Computerized Medical Imaging and Graphics 58 (2017) 75-85.

In step 260, the 3D geometry of the vessel is combined with the blood vessel wall displacement over time to form a 3D motion of the blood vessel. In other words, the information obtained from the tracking algorithm is combined with the 3D geometry of the vessel in a single coordinate system, which may then be provided to the biophysical model.

Figure 4:
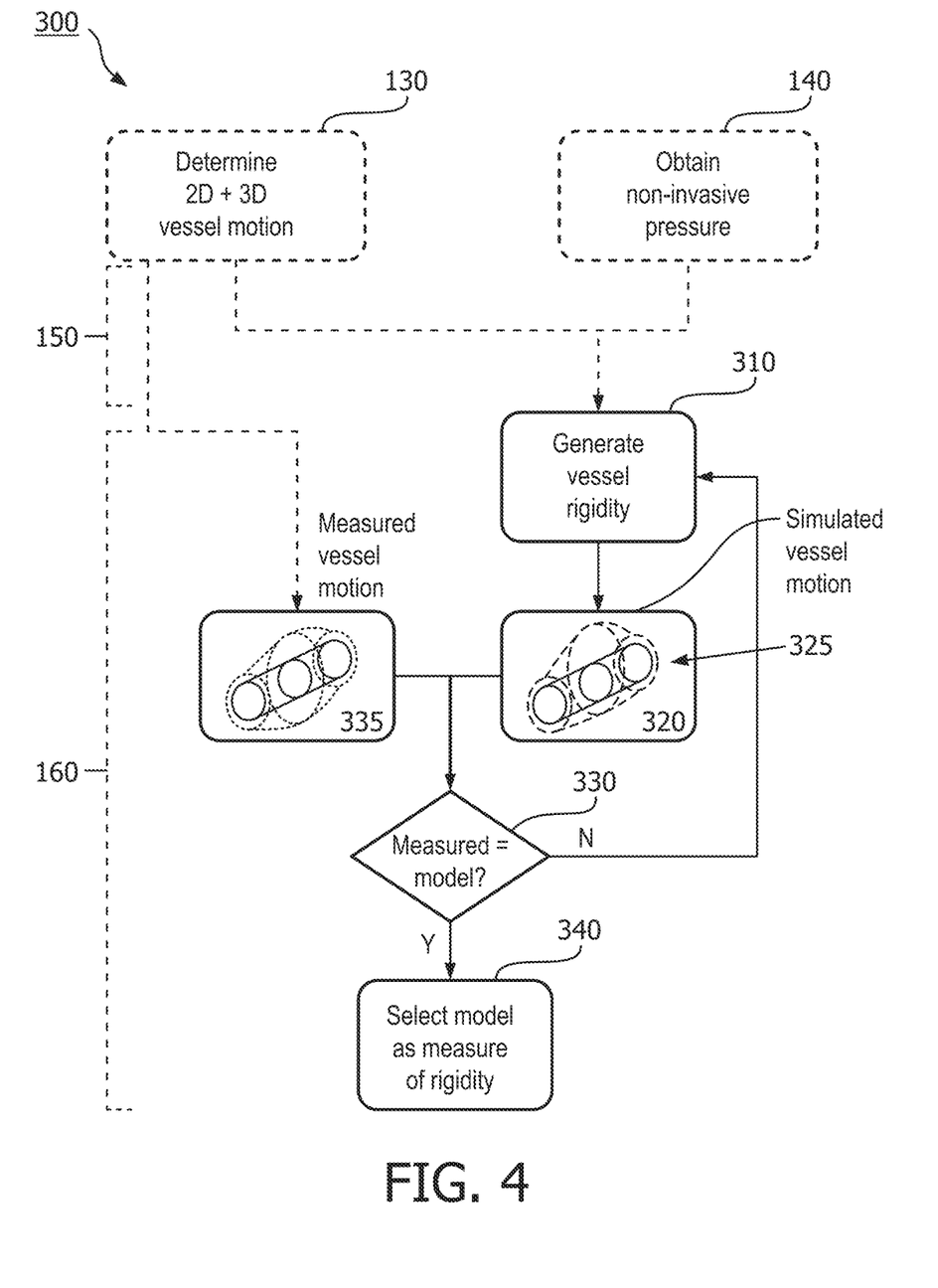
FIG. 4 shows a method for generating a measure of rigidity based on the biomechanical model.

FIG. 4 shows a method 300 for generating a measure of rigidity based on the biomechanical model. This method may be employed across steps 150 and 160 in FIG. 2 as described above.

In step 310, a test blood vessel rigidity is generated.

The test blood vessel rigidity is generated based on the non-invasive pressure measurement, the 3D features of the blood vessel taken from the 3D ultrasound data and wall displacement taken from the 2D ultrasound data.

In step 320, a test motion of the blood vessel 325 is simulated based on the test blood vessel rigidity.

The test motion is simulated by way of a 2D biophysics model with an embedded constitutive law, which may represent the relationship between the strain and stress of a material as described below with reference to FIG. 5. A constitutive law, or equation, is a relation between physical quantities that is specific to a given material or substance. Such a relationship may be used to approximate the response of a given material, such as a blood vessel wall, to an external stimuli. In the case of the blood vessel, the relation between parameters is the stress-strain relationship of the blood vessel wall, and in particular, its behavior in response to the external stimulus of a heartbeat.

In the present example, the constitutive law has a single parameter to estimate, which is the rigidity of the blood vessel; however, the biomechanical model may be employed to estimate a number of subject parameters of a different constitutive law.

In step 330, the test motion of the blood vessel is compared to the motion of the blood vessel 335.

If the test motion of the blood vessel matches the measured motion of the blood vessel, the method progresses to step 340 where the test blood vessel rigidity is selected as the measure of rigidity.

Further, an indicator of the vessel rigidity may then be provided to the physician who may then interpret the vessel rigidity and associated aneurism rupture risk.

Alternatively, if the test motion of the blood vessel does not match the measured motion of the blood vessel, the method returns to step 310 and the test blood vessel rigidity is adjusted.

Using a predefined constitutive law, such as a known relationship between stress and strain within a blood vessel, the biomechanical model estimation of the blood vessel rigidity is iteratively refined in order to match the extracted vessel motion, such as the vessel motion extracted in the method described above with reference to FIG. 2. At convergence, the model provides a personalized estimate of the vessel rigidity.

In other words, using the input from the image processing steps described above, the blood vessel rigidity estimation, or the estimation of any other suitable parameter by the biomechanical model, is performed iteratively. By comparing the simulated motion with the true measured motion, the vessel rigidity estimate may be adjusted and the processing is iterated until there is a good fit between the motion provided by the biophysical model and the measured motion of the vessel.

Such a method greatly reduces the computational costs required to generate a measure of aneurism rupture risk. More specifically, the proposed approach for biomechanical simulation may complete in a few minutes, thereby making the method usable in a clinical setup. In the literature, it has been reported that up to 2 weeks of calculation using finite-element methods is typically required to retrieve the mechanical properties from 3D ultrasound geometries. This time may be reduced to within 1 or 2 days if special parallelization approaches are available, such as those discussed in A. Wittek et al, "A finite element updating approach for identification of the anisotropic hyperelastic properties of normal and diseased aortic walls from 4D ultrasound strain imaging," *J. Mech. Behav. Biomed. Mater.*, no. June, 2015. However, such reported times are not practical for implementation in a daily clinical routine.

As the proposed approach for biomechanical simulation may be complete within a much shorter time period, it is practical for clinical implementation.

Figure 5:
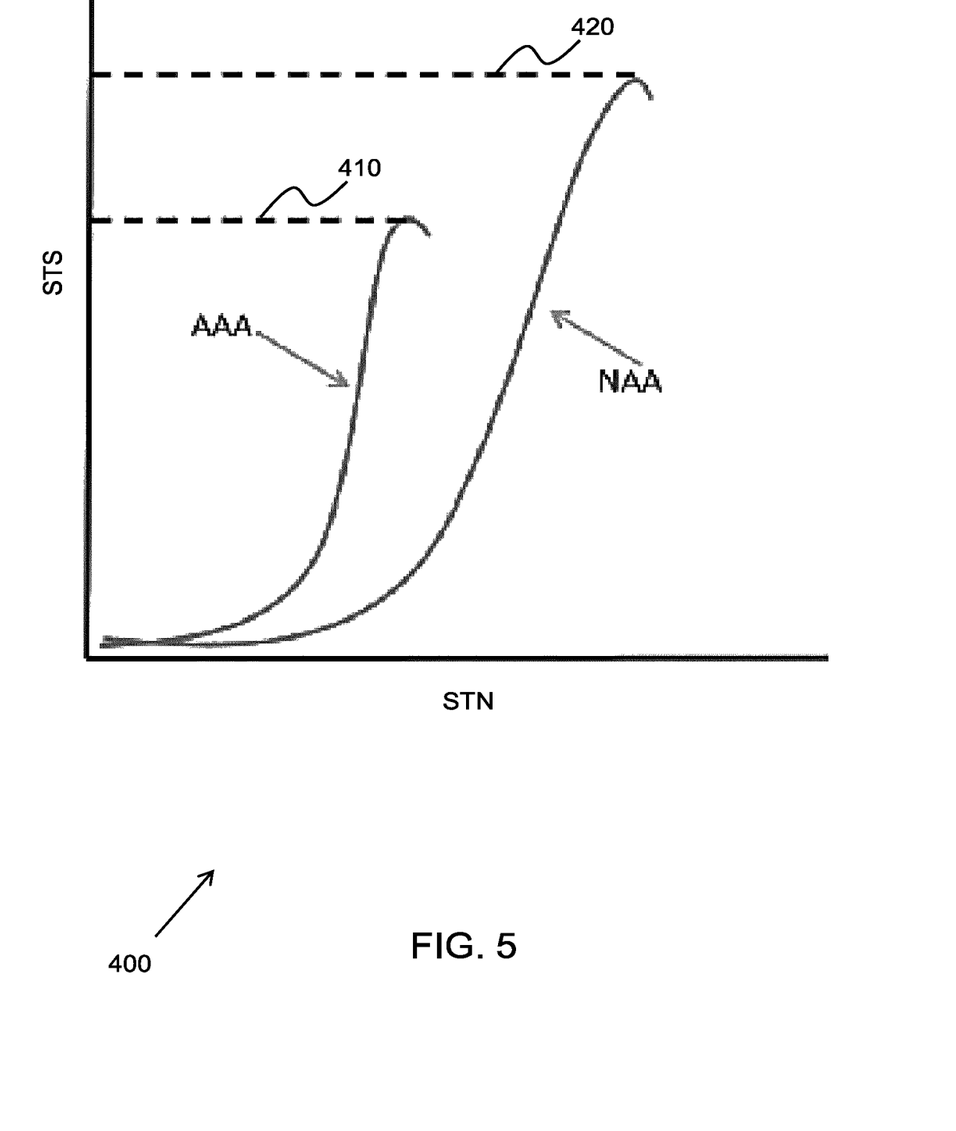
FIG. 5 shows a graph of stress against strain for a healthy blood vessel and an aneurism.

FIG. 5 shows a graph 400 of stress (STS) against strain (STN).

The graph includes a stress-strain curve for an abdominal aortic aneurism (AAA) and a stress-strain curve for a non-aneurysmal aorta (NAA). The peak of the curves represents the failure strength of the given vessel.

It can be seen from the gradient of the stress-strain curves that the abdominal aortic aneurism is stiffer than the non-aneurysmal aorta. Further, as can be seen from the graph, the failure strength of the abdominal aortic aneurism 410 is lower than the failure strength of the non-aneurysmal aorta 420. Aneurysms are stiffer than a healthy vessel and present a lower failure strength.

As described above, the constitutive law of the biomechanical model may be the relationship between the strain and stress of a material. For the example of the aorta, examples of constitutive laws that have been used include the Mooney-Rivlin law and Yeoh law.

Figure 6A:
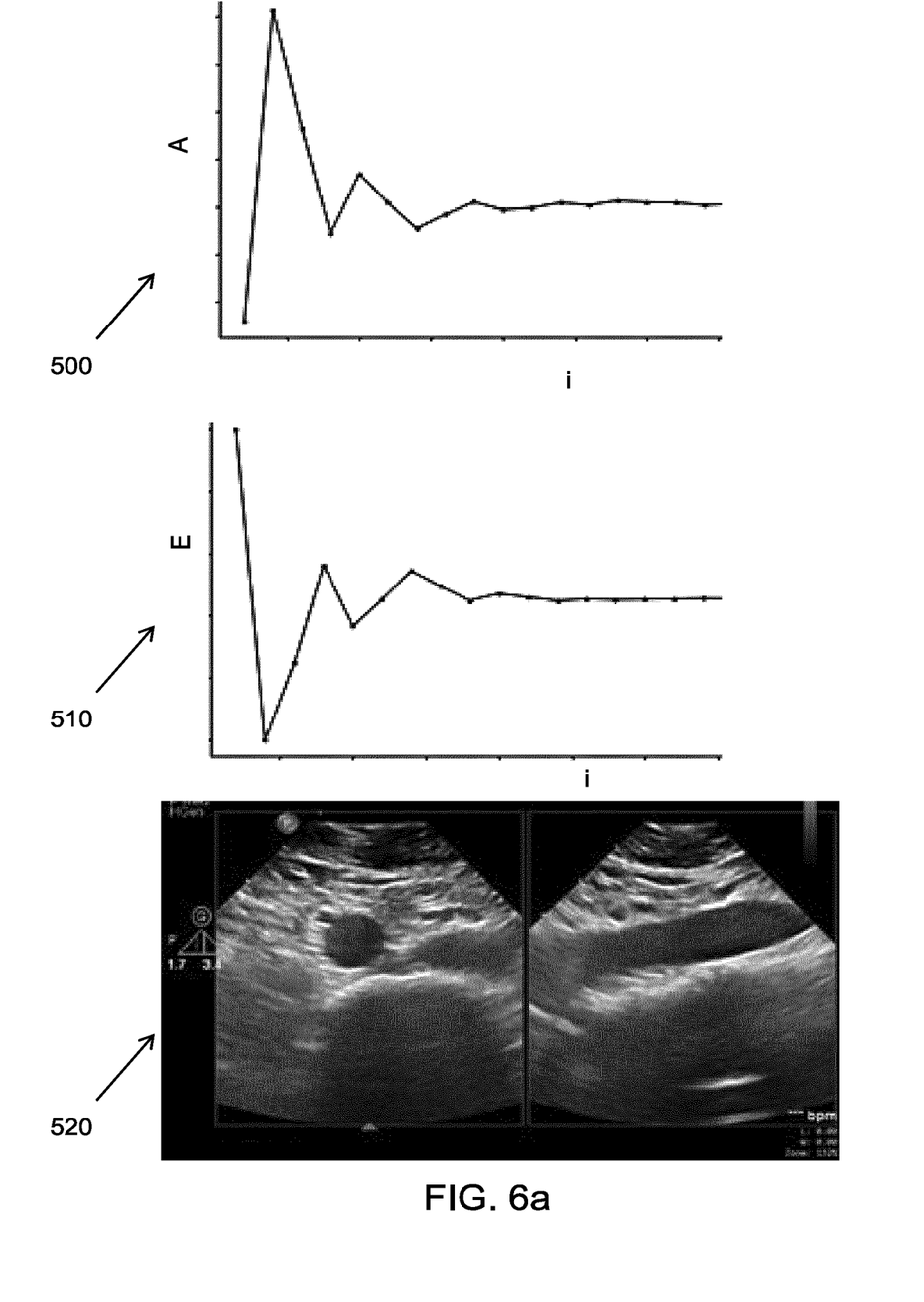
FIG. 6a and FIG. 6b show a comparison between results of the biomechanical model using data from a healthy vessel and an aneurism.
Figure 6B:
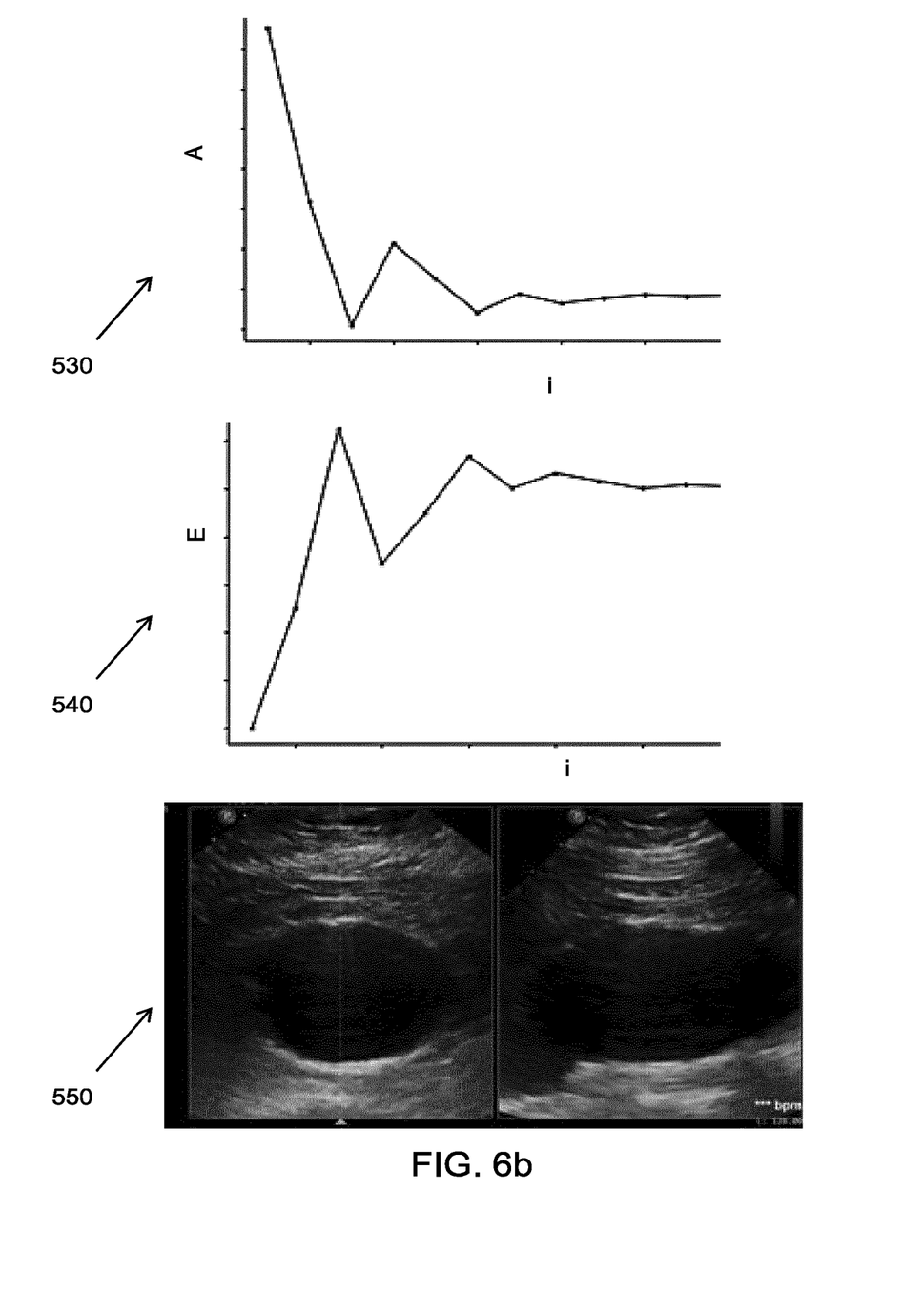

FIG. 6a and FIG. 6b show a comparison between results of the biomechanical model using data from a healthy vessel (FIG. 6a) and an aneurism (FIG. 6b).

FIG. 6a shows a graph 500 of vessel area, A, as measured from the 2D ultrasound data and the 3D ultrasound data, against the number of iterations, i, of the method described above with reference to FIG. 4.

Further, FIG. 6a shows a graph 510 of blood vessel rigidity, E, (or the Young's modulus of the vessel) against the number of iterations, i, of the method described above with reference to FIG. 4.

Finally, a bi-plane ultrasound image 520 of the vessel being investigated is included.

Looking to FIG. 6b, comparison graphs of vessel area against iterations 530 and blood vessel rigidity against iterations 540 and a comparison bi-plane image from an aneurism.

As can be directly seen from the bi-plane images 520 and 550, the area of the aneurism is significantly larger than that of the health vessel. It should be noted the scale of the graph of vessel area against iterations 500 for the healthy vessel is significantly smaller than the scale of the graph of vessel area against iterations for the aneurism.

The biomechanical model resulted in a vessel rigidity (Young's modulus) of 7.2 MPa obtained for a normal aorta and a vessel rigidity (Young's modulus) of 20 MPa for an aneurysmal aorta.

The measured vessel rigidity may then be used to assess a rupture risk for the aneurism.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. A method for generating a non-invasive measure of blood vessel rigidity for a subject, the method comprising:
   obtaining 2D ultrasound data of a blood vessel acquired from a first measurement location, wherein the 2D ultrasound data provides information relating to a movement of the blood vessel;
   obtaining 3D ultrasound data of the blood vessel acquired from the first measurement location, wherein the 3D ultrasound data provides information relating to a 3D geometry of the blood vessel, wherein the 2D ultrasound data and 3D ultrasound data are obtained from two separate ultrasound data acquisitions performed at said first measurement location;
   determining a motion of the blood vessel based on the movement of the blood vessel from the 2D ultrasound data;
   obtaining a non-invasive pressure measurement from the subject;
   providing the determined motion of the blood vessel, the 3D geometry of the blood vessel and the non-invasive pressure measurement to a biomechanical model; and
   generating a measure of rigidity of the blood vessel based on the biomechanical model.

2. The method as claimed in claim 1, wherein the 2D ultrasound data comprises bi-plane ultrasound data, wherein the bi-plane ultrasound data comprises:
   a first data plane representing a first orientation; and
   a second data plane representing a second orientation, the second orientation being orthogonal to the first orientation.

3. The method as claimed in claim 1, wherein the 2D ultrasound data comprises a plurality of data planes each representing a different location along a length of the blood vessel, wherein each data plane represents a blood vessel cross section of the blood vessel.

4. The method as claimed in claim 1, further comprising:
   obtaining additional 2D ultrasound data and/or additional 3D ultrasound data of another blood vessel from a second measurement location; and
   comparing the 2D ultrasound data and/or the 3D ultrasound data to the additional 2D ultrasound data and/or the additional 3D ultrasound data to provide a reference point for the blood vessel.

5. The method as claimed in claim 1, further comprising:
   generating a cineloop of the blood vessel based on the 2D ultrasound data, wherein the cineloop comprises a plurality of ultrasound image frames of the blood vessel, each acquired at a different moment during a cardiac cycle.

6. The method as claimed in claim 5, further comprising:
   applying a tracking algorithm to the cineloop, thereby delineating an initial blood vessel border for at least one of the plurality of ultrasound image frames of the blood vessel;
   for each of the plurality of ultrasound image frames, determining a blood vessel border based on the initial blood vessel border; and
   determining a blood vessel wall displacement over time of a blood vessel wall of the blood vessel based on the blood vessel border for each of the plurality of ultrasound image frames.

7. The method as claimed in claim 6, further comprising:
   determining a maximum blood vessel wall displacement and/or an average blood vessel wall displacement based on the blood vessel wall displacement over time.

8. The method as claimed in claim 1, further comprising:
   performing a spatial registration on the obtained 2D ultrasound data, and wherein the obtaining of the 3D ultrasound data is based on the spatial registration.

9. The method as claimed in claim 1, further comprising:
   segmenting a representation of the 3D geometry of the blood vessel from the 3D ultrasound data.

10. The method as claimed in claim 9, wherein the non-invasive pressure measurement comprises a brachial pressure index.

11. The method as claimed in claim 1, wherein generating of the measure of rigidity based on the biomechanical model comprises:

generating a test blood vessel rigidity;
simulating a test motion of the blood vessel based on the test blood vessel rigidity;
comparing the test motion of the blood vessel to the determined motion of the blood vessel;
when the test motion of the blood vessel matches the determined motion of the blood vessel, selecting the test blood vessel rigidity as the measure of rigidity; and
when the test motion of the blood vessel does not match the determined motion of the blood vessel, adjusting the test blood vessel rigidity.

12. A non-transitory computer medium storing computer program code that, when executed by at least one processor, causes the at least one processor to:
receive 2D ultrasound data of a blood vessel acquired from a first measurement location, wherein the 2D ultrasound data provides information relating to a movement of the blood vessel;
receive 3D ultrasound data of the blood vessel acquired from the first measurement location, wherein the 3D ultrasound data provides information relating to a 3D geometry of the blood vessel, wherein the 2D ultrasound data and 3D ultrasound data are obtained from two separate ultrasound data acquisitions performed at the first measurement location;
determining a motion of the blood vessel based on the movement of the blood vessel from the 2D ultrasound data;
obtain a non-invasive pressure measurement;
provide the determined motion of the blood vessel, the 3D geometry of the blood vessel and the non-invasive pressure measurement to a biomechanical model; and
generate a measure of rigidity of the blood vessel based on the biomechanical model.

13. A system for generating a non-invasive measure of blood vessel rigidity of a subject, the system comprising:
at least one processor; and
non-transitory memory storing code that, when executed by the at least one processor, causes the at least one processor to:
receive 2D ultrasound data of a blood vessel acquired from a first measurement location, wherein the 2D ultrasound data provides information relating to a movement of the blood vessel;
receive 3D ultrasound data of the blood vessel acquired from the first measurement location, wherein the 3D ultrasound data provides information relating to a 3D geometry of the blood vessel, wherein the 2D ultrasound data and 3D ultrasound data are obtained from two separate ultrasound data acquisitions performed at the first measurement location;
determine a motion of the blood vessel based on the movement of the blood vessel from the 2D ultrasound data;
obtain a non-invasive pressure measurement;
provide the determined motion of the blood vessel, the 3D geometry of the blood vessel and the non-invasive pressure measurement to a biomechanical model; and
generate a measure of rigidity of the blood vessel based on the biomechanical model.

14. The system as claimed in claim 13, further comprising:
an ultrasound system including an ultrasound probe, wherein the ultrasound probe is adapted to acquire the 2D ultrasound data and to acquire the 3D ultrasound data from the first measurement location.

15. The system as claimed in claim 14, further comprising:
a pressure measurement device adapted to acquire the non-invasive pressure measurement.

16. The method as claimed in claim 1, wherein the information relating to the movement of the blood vessel comprises information indicating a change in at least one of a shape of the blood vessel or a displacement of a blood vessel wall of the blood vessel.

17. The method as claimed in claim 1, wherein the biomechanical model comprises an embedded constitutive law representing a relationship between strain and stress of a blood vessel wall of the blood vessel.

18. The system as claimed in claim 15, wherein the pressure measurement device comprises a blood pressure cuff configured to provide a brachial pressure index.

19. The system as claimed in claim 13, wherein the 2D ultrasound data comprises bi-plane ultrasound data, wherein the bi-plane ultrasound data comprises:
a first data plane representing a first orientation; and
a second data plane representing a second orientation, the second orientation being orthogonal to the first orientation.

20. The system as claimed in claim 13, wherein the 2D ultrasound data comprises a plurality of data planes each representing a different location along a length of the blood vessel, wherein each data plane represents a blood vessel cross section of the blood vessel.

* * * * *